(12) United States Patent
Kopperschmidt

(10) Patent No.: US 8,430,834 B2
(45) Date of Patent: Apr. 30, 2013

(54) METHOD AND DEVICE FOR DETECTING AIR IN A FLUID SYSTEM, IN PARTICULAR IN AN EXTRACORPOREAL BLOOD CIRCUIT OF A BLOOD TREATMENT DEVICE

(75) Inventor: Pascal Kopperschmidt, Dittelbrunn (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 436 days.

(21) Appl. No.: 12/443,000

(22) PCT Filed: Sep. 25, 2007

(86) PCT No.: PCT/EP2007/008296
§ 371 (c)(1),
(2), (4) Date: Mar. 26, 2009

(87) PCT Pub. No.: WO2008/037409
PCT Pub. Date: Apr. 3, 2008

(65) Prior Publication Data
US 2009/0247926 A1    Oct. 1, 2009

(30) Foreign Application Priority Data

Sep. 26, 2006  (DE) .................. 10 2006 045 452

(51) Int. Cl.
*A61M 37/00* (2006.01)
(52) U.S. Cl.
USPC ........................................ 604/6.11; 604/4.01
(58) Field of Classification Search ........ 604/4.01–6.16, 604/27–29, 65–67; 600/485–487; 73/40, 73/40.5 A, 40.5 R, 593
See application file for complete search history.

(56) References Cited

U.S. PATENT DOCUMENTS

| 6,090,048 A * | 7/2000 | Hertz et al. ................... 600/485 |
| 2002/0174721 A1* | 11/2002 | Gross .............................. 73/592 |
| 2006/0257674 A1 | 11/2006 | Lipinski et al. |
| 2007/0108128 A1 | 5/2007 | Kopperschmidt et al. |

FOREIGN PATENT DOCUMENTS

| DE | 40 13 402 A1 | 11/1991 |
| DE | 100 33 192 A1 | 1/2002 |
| DE | 10355042 B3 | 6/2005 |
| JP | 2005-065888 | 3/2005 |
| JP | 2009-525585 | 8/2009 |
| WO | 98/00685 A2 | 1/1998 |

OTHER PUBLICATIONS

International Search Report, PCT/EP2007/008296, mailed Jan. 29, 2008.

* cited by examiner

*Primary Examiner* — Philip R Wiest
(74) *Attorney, Agent, or Firm* — Kenyon & Kenyon LLP

(57) ABSTRACT

The present invention relates to a method and to a device for detecting the entry of air in a fluid system, in particular in an extracorporeal blood circuit of a blood treatment device comprising an arterial branch leading to the blood treatment unit and a venous branch leading from said blood treatment unit. Periodic fluctuations in the fluid system, in particular in the arterial tube, are measured upstream of the blood pump arranged in said arterial tube. The measured periodic pressure signal is analyzed spectrally in a system of functions, in particular a system of orthogonal functions, for example sine and cosine functions and the entry of air is deduced if at least one of the coefficients of the functions exceeds or falls below predefined threshold values.

29 Claims, 2 Drawing Sheets

METHOD AND DEVICE FOR DETECTING AIR IN A FLUID SYSTEM, IN PARTICULAR IN AN EXTRACORPOREAL BLOOD CIRCUIT OF A BLOOD TREATMENT DEVICE

CROSS REFERENCE TO RELATED APPLICATIONS

This is a 371 national phase application of PCT/EP2007/008296 filed Sep. 25, 2007, claiming priority to German Patent Application No. 10 2006 045 452.9 filed Sep. 26, 2006.

FIELD OF INVENTION

The present invention relates to a method and arrangement for detecting the ingress of air into a system for liquid, and in particular into an extra-corporeal blood circuit of a blood-treating apparatus, which circuit has an arterial segment leading to a blood-treating unit and a venous segment exiting from the blood-treating unit. The present invention also relates to an extracorporeal blood-treating apparatus, and in particular a dialysis apparatus, having an arrangement for detecting an ingress of air into the extracorporeal blood circuit.

BACKGROUND OF THE INVENTION

In the field of medical technology, there are many known means by which liquids can be removed from patients, or liquids can be supplied to the patients, via a flexible tubing line. Access to the patient is generally obtained in this case via catheters for introduction into organs of the body or via needles or cannulas for insertion into vessels.

In methods for chronic blood-cleansing therapy such as hemodialysis, hemofiltration and hemodiafiltration, a patient's blood is passed through an extracorporeal blood circuit, which comprises an arterial segment leading to a blood-cleansing component in the form of a dialyser and a venous segment exiting from the dialyser. In the extracorporeal treatment of blood, there is a risk of air, which enters the blood circuit as a result of a leak, causing a life-threatening embolism in the patient. Air detectors, which are generally arranged in the venous segment of the blood circuit, are therefore used to monitor the extracorporeal blood circuit.

Methods of dialysis are known in which access to the patient is via a common needle which is connected to both the arterial and the venous segments of the blood circuit, or via two needles which are connected to the arterial segment and the venous segment, respectively, of the blood circuit.

In the single-needle method of dialysis, if there is a leak in the region of the needle, air may be drawn into the tubing during the arterial phase. Some of this air may be left in the tubing system in the region of the Y-connection between the arterial and venous segments, in which case there is a risk of some of this indrawn air being supplied straight to the patient in the venous phase without directly actuating the air detector in the venous segment. 20 ml of air, for example, may be drawn in during just one phase.

Depending on the cardiac output selected and the size of the dialyser, many phases may elapse before the air which is drawn in during the arterial phase is detected by the air detector in the venous segment of the blood circuit, and it is therefore possible that there may be a considerable delay in an error message being given.

The known monitoring systems for detecting air in the extracorporeal blood circuit sense changes in the optical, electrical or acoustic properties of the blood flowing in the extracorporeal blood circuit. If given limiting values are exceeded, an alarm is activated and any further circulation of the blood is stopped.

As well as the monitoring systems for detecting air, monitoring systems for detecting disruptions to the extracorporeal blood flow, such as stenoses for example, are also known.

DE 103 55 042 B3 describes a method of detecting disruptions to the blood flow in which the phase angle of at least one upper harmonic of an oscillating pressure signal propagating in the extracorporeal blood circuit is determined, disruptions to the blood flow being detected on the basis of a characteristic change in the phase angle of at least one upper harmonic of the pressure signal. A precondition set by the known method is that the blood pump must generate an oscillating pressure signal in the blood circuit.

Known from US Publication No. 2002/0174721 A1 is a method of detecting stenoses in a flexible tubing system during extracorporeal treatment of blood. To allow a stenosis to be detected, the frequency spectrum of an oscillating pressure signal, which is attributable to the operation of the blood pump and which propagates in the extracorporeal blood circuit, is analyzed. It is concluded that a stenosis exists if the attenuation of at least one upper harmonic of the oscillating pressure signal changes.

DE 100 33 192 A1 describes a method of detecting arterial input problems during extracorporeal blood treatment, in which the amplitude of cyclic variations in pressure in the venous blood line is measured and compared with a limiting value. It is concluded that there arterial input problems exist if the limiting value is exceeded. A precondition set by the known method is that the blood pump must produce cyclic variations in pressure in the blood circuit.

SUMMARY OF THE INVENTION

The object underlying the present invention is to specify a method by which the ingress of air into a system for liquid, and in particular into the extracorporeal blood circuit of a blood-treating apparatus, can be identified with high reliability. A further object of the present invention is to provide an arrangement which allows an ingress of air into a system for liquid, and in particular an extracorporeal blood circuit, to be detected with high reliability. It is also an object of the present invention to provide an extracorporeal blood-treating apparatus having an arrangement for detecting an ingress of air into the extracorporeal blood circuit with high reliability.

In the method according to the present invention and the arrangement according to the present invention, cyclic variations in pressure in the system for liquid are measured and analysed. The method according to the present invention and the arrangement according to the present invention are based on the spectral breakdown of the cyclic pressure signal measured into a system of functions, in which case the coefficients of the functions are monitored. It is concluded that the ingress of air into the system for liquid has taken place if at least one of the coefficients of the functions exceeds or drops below preset limiting values.

In tests, it has been found that air which makes its way into a system for liquid, such as, for example, the air which makes its way into an extracorporeal blood circuit of a blood-treating apparatus, causes small variations in pressure whose amplitude is too small to cause the preset limiting values of the pressure monitoring systems which are generally present in pieces of blood-treating apparatus to be exceeded or dropped below. However, spectral breakdown of the cyclic pressure signal allows variations in pressure of this kind to become clear. Thus, it is possible even for only small amounts of air which make their way into the system for liquid, in particular the extracorporeal blood circuit of a blood-treating apparatus, in particular a dialysis apparatus, to be detected with high reliability.

In the case of a system for liquid which has a segment in which a pump for pumping the liquid is arranged, the cyclic variations in pressure are measured upstream of the pump in the segment of the system for liquid. The segment of the system for liquid in which the cyclic variations in pressure are measured may be a line carrying the liquid.

It is enough for only one of the coefficients of the functions to be monitored. However, the reliability with which an ingress of air is detected may be increased by monitoring a plurality of coefficients of the functions. It can then be concluded that there has been an ingress of air if all of the plurality of coefficients of the functions exceed or drop below the preset limiting values.

The preset limiting values preferably define a limiting value range having an upper and a lower limiting value, the coefficients of the functions each being compared with the given upper and lower limiting values.

The method according to the present invention and arrangement according to the present invention preferably make provision for the breakdown of the cyclic pressure signal into a system of orthogonal complex functions or complex conjugate functions, for example into a system of sine and cosine functions.

The detection of the ingress of air on the basis of the spectral breakdown of the cyclic pressure signal into a system of functions has advantages particularly for the detection of an ingress of air into the arterial segment of the extracorporeal blood circuit of an extracorporeal blood-treating apparatus using the single-needle method of dialysis. To detect an ingress of air into the extracorporeal blood circuit, the variations in pressure are preferably measured and analysed in the arterial segment of the extracorporeal blood circuit, upstream of the blood pump, which is generally arranged in the said arterial segment. With the single-needle method of dialysis, an ingress of air into the extracorporeal blood circuit may thus take place even upstream of the blood pump, and the pumping of the blood can thus be stopped and an audio and/or visual alarm can thus be tripped to indicate an ingress of air within a fraction of a phase. An ingress of air into the arterial segment can also be detected in the case of the two-needle method of dialysis. The detection of an ingress of air may also be used as an indicator of the generation of micro-bubbles, which are generally detected in known pieces of blood-treating apparatus by an air detector in the venous segment of the extracorporeal blood circuit.

BRIEF DESCRIPTION OF THE DRAWINGS

In what follows, an embodiment of the invention will be explained in detail by reference to the drawings. In the drawings.

DETAILED DESCRIPTION OF THE DRAWINGS

Figure 1:
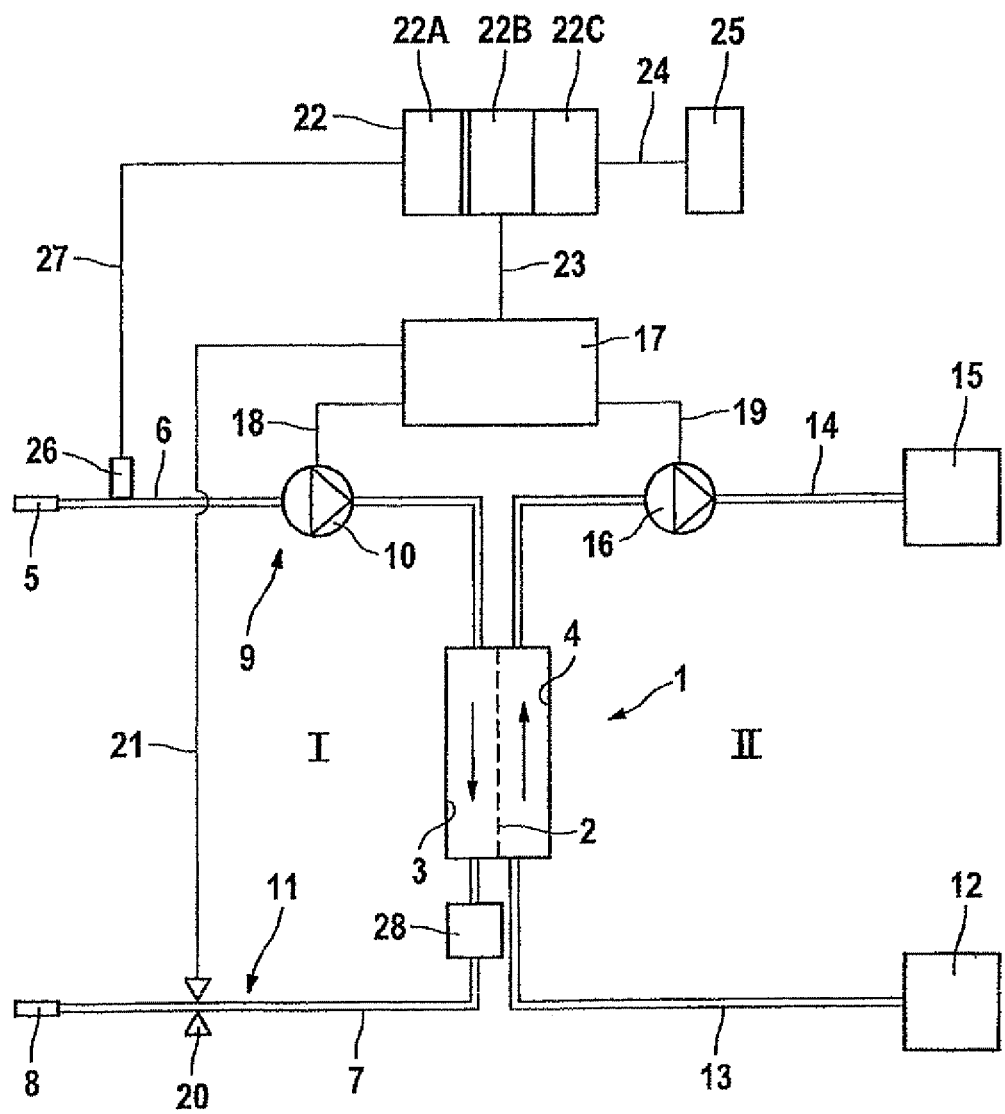
FIG. 1 is a highly simplified schematic view showing the principal components of a blood-treating apparatus together with an arrangement for detecting the ingress of air into the extracorporeal blood circuit.

FIG. 1 shows the principal components of an extracorporeal blood-treating apparatus, a hemodialysis apparatus in the present embodiment, which has an arrangement for detecting the ingress of air into the extracorporeal blood circuit, and in particular into the arterial segment of the extracorporeal blood circuit. The hemodialysis apparatus has a dialyser 1 which is divided by a semi-permeable membrane 2 into a blood chamber 3 and a chamber 4 for dialysis fluid. Connected to the patient's vascular system by means of an arterial puncture needle 5 is an flexible arterial tubing line 6 which runs to the inlet of the blood chamber 3 of the dialyser 1. Exiting from the outlet of the blood chamber 3 of the dialyser 1 is a flexible venous tubing line 7 which is connected to the patient's vascular system by means of a venous puncture needle 8. Arranged in the arterial segment 9 of the extracorporeal blood circuit I is an occluding blood pump 10, in particular a peristaltic pump, while arranged in the venous segment 11 of the extracorporeal blood circuit I is a bubble trap 28 such as, for example, a drip chamber.

The dialysis apparatus being described is a dialysis apparatus for the two-needle method of dialysis. A dialysis apparatus for the single-needle method of dialysis differs from a two-needle dialysis apparatus only in that the arterial and venous blood lines are brought together by means of a Y-connection, the blood being removed from and supplied to the patient through only one needle in successive phases. Additionally, the single-needle dialysis apparatus may also have a balancing chamber, which is arranged downstream of the arterial blood pump 10, and a further blood pump which is arranged downstream of the balancing chamber in the arterial segment 9 of the extracorporeal blood circuit I.

In what follows, the invention will be described by reference to the two-needle dialysis apparatus, with cyclic variations in pressure being measured and analysed upstream of the arterial blood pump 10. Also in the case of the single-needle dialysis apparatus, the cyclic variations in pressure are measured upstream of the arterial blood pump 10.

The dialysis-fluid circuit II of the hemodialysis apparatus comprises a dialysis-fluid source 12, to which is connected a dialysis-fluid inlet line 13 which runs to the inlet of the dialysis-fluid chamber 4 of the dialyser 1. Exiting from the outlet of the dialysis-fluid chamber 4 of the dialyser 1 is a dialysis-fluid outlet line 14 which runs to an outlet 15. Connected into the dialysis-fluid outlet line 14 is a pump 16 for dialysis fluid.

A central control unit 17 controls the dialysis apparatus, which operates the pumps 10, 16 for blood and dialysis fluid via control lines 18, 19. Downstream of the blood chamber 3 of the dialyser 1, on the venous flexible tubing line 7 is an electromagnetically actuatable tube clamp 20, which is closed by the central control unit 17 via a further control line 21 if the ingress of air into the extra-corporeal blood circuit is detected. The control unit 17 also stops the blood pump 10. To enable an ingress of air to be detected, the dialysis apparatus also has an arrangement 22 which communicates with the central control unit 17 via a data line 23. The arrangement 22 for detecting an ingress of air is connected via a further data line 24 to an alarm unit 25 which emits a visual and/or audio alarm in the event of an ingress of air. If there is an ingress of air, the arrangement 22 also actuates the central control unit 17, which then closes the venous tube clamp 20 and stops the blood pump 10.

In what follows, the method according to the invention of detecting an ingress of air, and the construction and operation of the arrangement for detecting an ingress of air, will be described in detail.

The arrangement 22 has means 22A for measuring the pressure in the arterial segment 9 of the extracorporeal blood circuit I upstream of the arterial blood pump 10. The pressure is measured by means of a pressure sensor 26 which is arranged, in the arterial flexible tubing line 6, upstream of the arterial blood pump 10 and which is connected to the arrangement 22 via a data line 27. In the event of a possible ingress of air due to a leak, caused for example by leaking tubing connections, evidence may be found of changes in the cyclic variations in pressure produced by the blood pump 10 in the arterial segment 9 of the extracorporeal blood circuit I upstream of the blood pump 10.

The arrangement 22 has means 22B, 22C for analysing the cyclic pressure cycle that is measured, to determine if there has been a possible ingress of air. The means 22B, 22C for analyzing the cyclic pressure signal comprise means 22B for the spectral breakdown of the pressure signal into a system of functions. The means 22B for breaking down the cyclic pressure signal breaks down the pressure signal $P_{art}(t)$ into a system of orthogonal functions, which in the present embodiment are sine functions and cosine functions.

Basically, what applies to the algorithm for monitoring air is a breakdown of the cyclic pressure signal $P_{art}(t)$ into frequency-dependent coefficients $p(\omega)$. The basic system is set by the orthogonal complex functions $f(\omega,t)$ or complex conjugate functions $f'(\omega,t)$ $$P_{art}(t)=\int f(\omega,t) \cdot p(\omega) d\omega \quad \text{[Equation 1]}$$

Example of an orthogonal basic system:

$$f(\omega,t)=e^{i\omega t}; \int f(\omega,t) \cdot f^*(\omega',t)=\delta(\omega'.\omega) \quad \text{[Equation 2]}$$

Given equations 1 and 2, the coefficients $p(\omega)$ are calculated from:

$$\int f^*(\omega,t) \cdot P_{art}(t) d\omega = \int f^*(\omega,t) \cdot \int f(\omega',t) \cdot p(\omega') d\omega' d\omega = p(\omega') \delta(\omega',\omega)=p(\omega). \quad \text{[Equation 3]}$$

Other systems may also be used as well as the basic system specified under equation 2.

The frequency-dependent coefficients $p(\omega)$ are stable over time provided the cycle frequency of the arterial pressure signal is congruent with the frequency ω of the algorithm. The coefficients become unstable as soon as there are added disruptions which are not phase-correlated with the cycle frequency of the arterial pressure signal. These disruptions may be spontaneous intakes of air into the arterial flexible tubing system upstream of the arterial pressure sensor.

Figure 2:
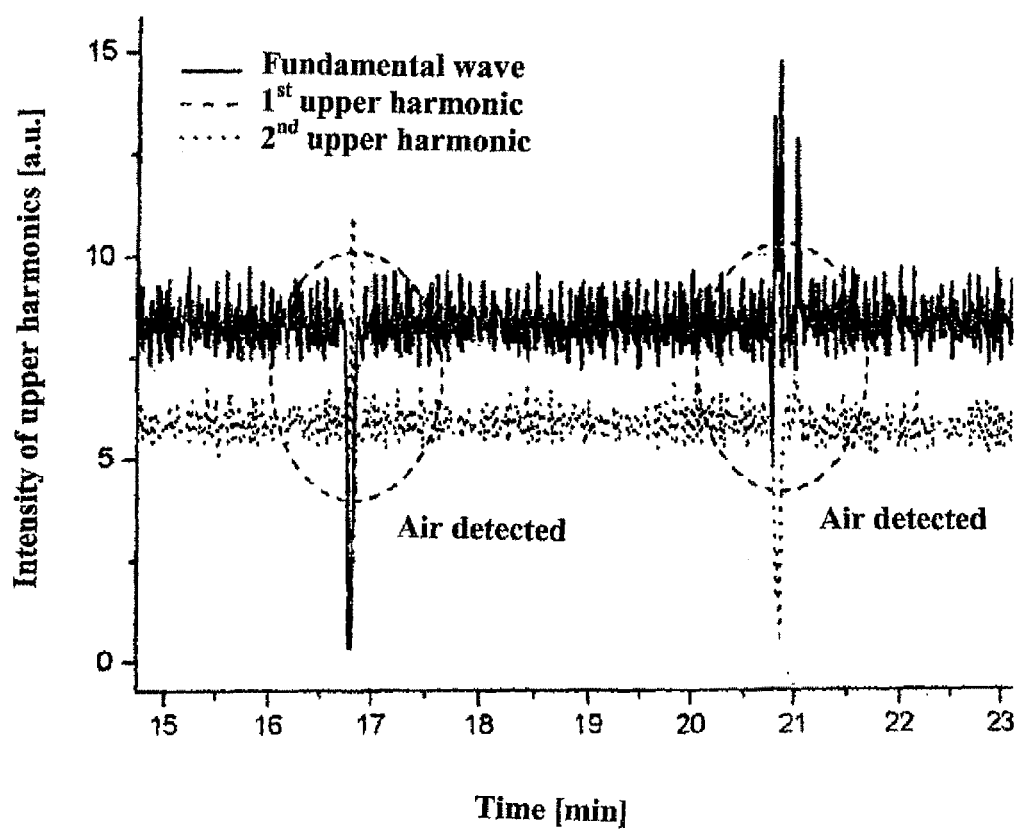
FIG. 2 shows, as a function of time, the intensity of the fundamental wave of the cyclic pressure signal, which is measured and of its first and second upper harmonics.

FIG. 2 shows the amplitude of the fundamental wave and of the first two upper harmonics in the event of a spontaneous ingress of 1-2 ml of air on the arterial side at the time of an in vitro dialysis treatment. The three coefficients $p(\omega 1)$, $p(\omega 2)$ and $p(\omega 3)$ of the spectral breakdown of the cyclic pressure signal can be seen, i.e. the fundamental wave and the first and second upper harmonics. The coefficients are stable over time provided there is not a disruption. Disruptions produced by air that has made its way into the arterial segment of the tubing cause an instability in the coefficients, as can be seen from FIG. 2. Behaviour in the event of the instability depends on the amount and effect of the air taken in. In the present case it is the intensity of the coefficients which is monitored. It is however equally possible for the phase of the coefficients to be monitored rather than their intensity.

It has been found that, after a change in at least one or a plurality of the coefficients due to an ingress of air, i.e. if the at least one or the plurality of the coefficients have risen about a preset limiting value or have dropped below a preset limiting value, the at least one or the plurality of the coefficients return to their original value or drop or rise by a value whose amount is less than the amount of the change. The tendency to return to the original values may advantageously be used as an additional criterion for detecting the ingress of air because the air that enters does not distribute itself uniformly in the system for liquid. What, in fact, arise are alternating larger and smaller proportions of air in the liquid. For this purpose, the change in the measured values is monitored and after a preset period from the occurrence of the change, a check is made to see whether at least one of the coefficients is larger or smaller than a preset limiting value, which is larger or smaller by a given amount than, respectively, the preset lower or upper limiting value for the monitoring of the coefficients.

The means 22B, 22C for analyzing the cyclic pressure signal also comprise means 22C for monitoring the coefficients $p(\omega)$ of the sine and cosine functions.

The detection of an instability resulting from an ingress or air is made possible by setting a limiting value range $crit_i$ around the value of the $i^{th}$ coefficient $p(\omega_i)$. If this limiting value is exceeded or dropped below, the instability is detected and it is thus concluded that there has been an ingress of air.

$$|p(\omega_i)|>crit_i; i=1, 2, 3 \ldots N. \quad \text{[Equation 4]}$$

The intensity of the fundamental wave and of the first and second harmonics (i=1, 2, 3) is monitored, for example. For this purpose, the particular coefficient $p(\omega_i)$ is compared with an upper and a lower limiting value, it being concluded if the upper limiting value is exceeded or the lower limiting value is dropped below that there has been an ingress of air. In the event of an ingress of air, the blood pump 10 is stopped, the tube clamp 20 is closed and an audio and/or visual alarm is given. In addition, it can be monitored whether at least one of the coefficients has again reached a preset value on expiry of a preset period of time, in which case an alarm is only given in this event and otherwise it is not concluded that there has been an ingress of air.

The possibility of false alarms is preferably ruled out by its only being concluded that there has been an ingress of air if all the coefficients are outside the defined limiting value range, i.e. are larger or smaller than, respectively, the upper or lower limiting value. As the number of coefficients becomes larger so does the likelihood of false alarms become smaller.

As can be seen from FIG. 2, the coefficients vary about a value $p_{ref}(\omega_i)$ which must not be zero. The respective values for the individual components can be stored as constants in the means 22C for monitoring the coefficients. It is useful however for the values to be determined continuously during application as averages over time windows, so that they are adjusted to the conditions at the time.

The following criterion, from which it is concluded that there has been an ingress of air, is thus obtained:

$$|p(\omega_i)-p_{ref}(\omega_i)|>crit_i; i=1, 2, 3 \ldots N \quad \text{[Equation 5]}$$

It is also possible for relative limiting values to be set rather than absolute ranges, in which case different criteria may apply to the upper and lower limiting values. In this case, the sign of the difference, which is specified between the amount terms in the equation, would also need to be allowed for when the values were being analyzed.

What is claimed is:

1. A method for detecting the ingress of air into a system for liquid comprising:
   measuring and analyzing a pressure signal in the liquid;
   spectrally breaking down the measured pressure signal into at least one function, said at least one function having at least one coefficient;
   monitoring the at least one coefficient of the at least one function;
   comparing the at least one coefficient of the at least one function to respective preset limiting values; and determining that there has been an ingress of air into the system for liquid if at least one of the coefficients of the at least one function exceeds or drops below the respective preset limiting values.

2. The method according to claim 1, wherein the at least one function is a system of orthogonal functions.

3. The method according to claim 2, wherein the orthogonal functions are sine functions and cosine functions.

4. The method according to claim 1, wherein the respective preset limiting values define a limiting value range having an upper limiting value and a lower limiting value, the method further comprising:
determining there has been an ingress of air into the system for liquid if at least one of the coefficients of the at least one function exceeds the upper limiting value or drops below the lower limiting value.

5. The method according to claim 4, wherein a plurality of coefficients of the at least one function are each compared with an upper and a lower limiting value, the method further comprising:
determining there has been an ingress of air into the system for liquid if all of the plurality of coefficients of the at least one function exceed the upper limiting value or drop below the lower limiting value.

6. The method according to claim 5, wherein the at least one function is a plurality of functions, the method further comprising:
determining there has been an ingress of air into the system for liquid if the plurality of coefficients of the plurality of the functions exceed the upper limiting value or drop below the lower limiting value.

7. The method according to claim 1, wherein the system comprises a pump, the method further comprising: measuring the pressure signal upstream of the pump.

8. The method according to claim 7, wherein the pump is located in a conduit, further comprising: measuring the pressure signal in the conduit.

9. The method according to claim 1, wherein the system comprises an extra-corporeal blood circuit of a blood-treating apparatus comprising: an arterial segment leading to the blood-treating unit and a venous segment leading from the blood-treating unit, the method further comprising: measuring and analyzing the pressure signal in the arterial segment or the venous segment of the extra-corporeal blood circuit.

10. The method according to claim 9, wherein a blood pump is located in the arterial segment, the method further comprising:
measuring the pressure signal in the arterial segment, upstream of the blood pump.

11. A system for detecting the ingress of air into a system for liquid, comprising:
means for measuring a pressure signal in the system for liquid; and
means for analyzing the measured pressure signal comprising:
means for spectrally breaking down the measured pressure signal into at least one function, said at least one function having at least one coefficient; and
means for monitoring the at least one coefficient of the at least one function and comparing the at least one coefficient to respective preset limiting values, configured such that an ingress of air into the system for liquid is determined if at least one of the coefficients of the at least one function exceeds or drops below the respective preset limiting values.

12. The system according to claim 11, wherein the at least one function is a system of orthogonal functions.

13. The system according to claim 12, wherein the orthogonal functions are sine functions and cosine functions.

14. The system according to claim 11, wherein the means for monitoring further comprises:
means for comparing configured such that at least one of the coefficients is compared with an upper limiting value and a lower limiting value, and an ingress of air into the system for liquid is determined if the at least one coefficient of the at least one function exceeds the upper limiting value or drops below the lower limiting value.

15. The system according to claim 14, wherein the means for comparing are configured such that a plurality of coefficients of the at least one function are each compared with an upper limiting value and a lower limiting value, and an ingress of air into the system for liquid is determined if all of the plurality of coefficients of the functions exceed the upper limiting value or drop below the lower limiting value.

16. The system according to claim 11, further comprising a pump, wherein the means for measuring pressure is located upstream of the pump.

17. The system according to claim 16, wherein the pump is located in a conduit and the means for measuring pressure measures pressure in the conduit.

18. The system according to claim 11 wherein the system further comprises:
an extra-corporeal blood circuit of an extra-corporeal blood-treating apparatus comprising an arterial segment leading to a blood-treating unit and a venous segment leading from the blood-treating unit, the means for measuring pressure being located in the arterial segment or the venous segment of the extra-corporeal blood circuit.

19. The system according to claim 18, further comprising a blood pump located in the arterial segment, wherein the means for measuring pressure is located upstream of the blood pump.

20. An extra-corporeal blood-treating apparatus comprising: an extra-corporeal blood circuit which has an arterial segment leading to a blood-treating unit and a venous segment leading from the blood-treating unit, wherein the blood-treating apparatus has a system for detecting the ingress of air into the extra-corporeal blood circuit comprising:
means for measuring a pressure signal in the system for liquid; and
means for analyzing the measured pressure signal comprising:
means for spectrally breaking down the measured pressure signal measured into at least one function, said at least one function having at least one coefficient;
means for monitoring the at least one coefficient of the at least one function and comparing the at least one coefficient to respective preset limiting values, configured such that an ingress of air into the system for liquid is determined if at least one of the coefficients of the at least one function exceeds or drops below the respective preset limiting values.

21. A system for detecting the ingress of air into a system for liquid, comprising:
a measurement system configured to measure a pressure signal in the system for liquid; and
an analysis system configured to analyze the measured pressure signal comprising:
a function system configured to spectrally break down the measured pressure signal into at least one function, said at least one function having at least one coefficient; and
a monitoring system configured to monitor the at least one coefficient of the at least one function and compare the at least one coefficient to respective preset limiting values, wherein the monitoring system is configured such that an ingress of air into the system for liquid is determined if at least one of the coefficients of the at least one function exceeds or drops below the respective preset limiting values.

22. The system according to claim 21, wherein the at least one function is a system of orthogonal functions.

23. The system according to claim 22, wherein the orthogonal functions are sine functions and cosine functions.

24. The system according to claim 21, wherein the monitoring system further comprises:
a comparison system configured such that at least one of the coefficients is compared with an upper limiting value and a lower limiting value, and an ingress of air into the system for liquid is determined if the at least one coefficient of the at least one function exceeds the upper limiting value or drops below the lower limiting value.

25. The system according to claim 24, wherein the comparison system is configured such that a plurality of coefficients of the at least one function are each compared with an upper limiting value and a lower limiting value, and an ingress of air into the system for liquid is determined if all of the plurality of coefficients of the functions exceed the upper limiting value or drop below the lower limiting value.

26. The system according to claim 21, further comprising a pump, wherein the measurement system is located upstream of the pump.

27. The system according to claim 26, wherein the pump is located in a conduit and the measurement system measures pressure in the conduit.

28. The system according to claim 21 wherein the system further comprises:
an extra-corporeal blood circuit of an extra-corporeal blood-treating apparatus comprising an arterial segment leading to a blood-treating unit and a venous segment leading from the blood-treating unit, the measurement system being located in the arterial segment or the venous segment of the extra-corporeal blood circuit.

29. The system according to claim 28, further comprising a blood pump located in the arterial segment, wherein the measurement system is located upstream of the blood pump.

* * * * *

UNITED STATES PATENT AND TRADEMARK OFFICE
CERTIFICATE OF CORRECTION

PATENT NO. : 8,430,834 B2  Page 1 of 1
APPLICATION NO. : 12/443000
DATED : April 30, 2013
INVENTOR(S) : Pascal Kopperschmidt It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 539 days.

Signed and Sealed this
Eighth Day of September, 2015

Michelle K. Lee
*Director of the United States Patent and Trademark Office*